United States Patent

Fauland et al.

[11] 3,982,012
[45] Sept. 21, 1976

[54] 4-HYDROXY-BENZIMIDAZOLE COMPOUNDS AND THERAPEUTIC COMPOSITIONS

[75] Inventors: Erich Fauland, Mannheim-Gartenstadt; Wolfgang Kampe, Heddesheim; Max Thiel, Mannheim; Wolfgang Bartsch, Viernheim; Wolfgang Schaumann, Heidelberg, all of Germany

[73] Assignee: Boehringer Mannheim G.m.b.H., Mannheim, Germany

[22] Filed: June 10, 1975

[21] Appl. No.: 585,645

[30] Foreign Application Priority Data
July 5, 1974 Germany............................ 2432269

[52] U.S. Cl............................ 424/273; 260/309.2; 260/570.7
[51] Int. Cl.²..................................... C07D 235/08
[58] Field of Search.................. 260/309.2; 424/273

[56] References Cited
OTHER PUBLICATIONS
Kasuya et al., Chem. Abst. 1973, vol. 79, No. 137129z.
Troxler, Chem. Abst. 1969, vol. 71, No. 70493c.

*Primary Examiner*—Natalie Trousof
*Attorney, Agent, or Firm*—Burgess, Dinklage & Sprung

[57] ABSTRACT

New 4-hydroxy-benzimidazole compounds of the formula:

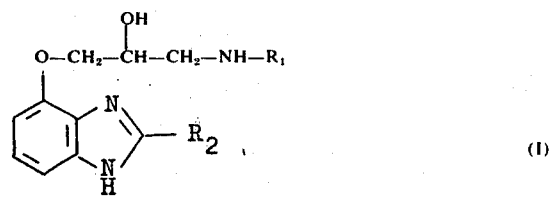

wherein
$R_1$ is straight-chained or branched alkyl and
$R_2$ is hydrogen atom or lower alkyl
and the pharmacologically compatible salts thereof; are outstandingly effective in the treatment and prophylaxis of cardiac and circulatory diseases, and provide substantially greater margins of safety than prior art adrenergic β-receptor inhibitors.

14 Claims, No Drawings

4-HYDROXY-BENZIMIDAZOLE COMPOUNDS AND THERAPEUTIC COMPOSITIONS

The present invention relates to new basic-substituted derivatives of 4-hydroxy-benzimidazole and to therapeutic compositions and methods utilizing same.

The new 4-hydroxy-benzimidazole compounds of the invention are of the formula:

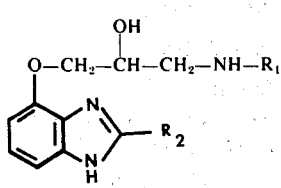

(I)

wherein
$R_1$ is straight-chained or branched alkyl and
$R_2$ is hydrogen atom or lower alkyl
and the pharmacologically compatible salts thereof.

The alkyl radicals $R_1$ are preferably branched and can contain up to 6 carbon atoms and preferably contain 3 or 4 carbon atoms. The alkyl radical $R_2$ can contain up to 3 carbon atoms, methyl being preferred.

The new compounds of general formula (I) and their pharmacologically compatible salts bring about an inhibition of adrenergic β-receptors and are, therefore, suitable for the treatment and prophylaxis of cardiac and circulatory diseases.

The new compounds (I) according to the present invention can be repared, for example, by one of the following methods:

a. reaction of a compound of the general formula:

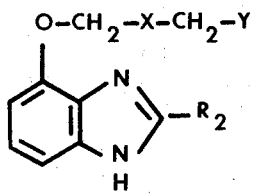

(II)

with a compound of the general formula:

 (III)

wherein $R_1$ and $R_2$ have the same meanings as above, one of the symbols Y and Z stands for an amino group and the other for a reactive residue and X is a >C=O or >CH—A group, in which A is a hydroxyl group or, together with Y, can also represent an oxygen atom, and, when X is a >C=O group, the product obtained is subsequently reduced; or b. reaction of a compound of the general formula:

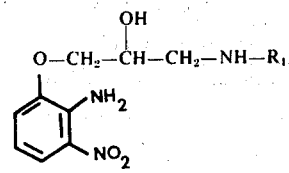

(IV)

wherein $R_1$ has the same meaning as above, with a compound of the general formula:

 (V)

wherein $R_2$ has the same meaning as above; whereafter, if desired, the compound obtained is converted into a pharmacologically compatible salt.

The reactive residues Y and Z in compounds of general formulae (II) and (III) are preferably acid residues, for example, residues of hydrohalic or sulfonic acids.

The reaction of compounds of general formula (II) with compounds of general formula (III) according to process (a) is preferably carried out in an organic solvent which is inert under the reaction conditions used, for example, in ethanol, n-butanol, dioxane or dimethyl formamide. The reaction can also be carried out by mixing equimolar amounts of the reaction components and leaving the mixture to stand at ambient temperature or by heating.

When the reduction of the >C=O group has to be carried out, it can be accomplished by catalytic hydrogenation or by means of some other appropriate reducing agent, for example, a complex metal hydride, such as sodium borohydride. However, it is preferable to employ catalytic hydrogenation using known catalysts, for example noble metal catalysts or nickel catalysts in conventional solvents, such as ethanol or dioxane.

The compounds of general formula (IV) can be prepared by the reduction of compounds of the general formula:

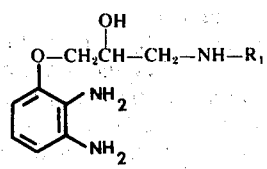

(IV)

wherein $R_1$ has the same meaning as above, the reduction preferably being carried out by catalytic hydrogenation. The crude o-phenylene-diamine derivative of general formula (IV) which are hereby formed are advantageously used as starting materials, without further purification, for process (b), either as the free bases or as salts with mineral acids. The cyclization is preferably carried out by heating with an excess of compounds of general formula (V).

The compounds of general formula (I) can be converted into their pharmacologically compatible salts by reaction, preferably in an organic solvent, with an equivalent amount of an inorganic or organic acid, for example, with hydrochloric acid, hydrobromic acid, phosphoric acid, sulfuric acid, acetic acid, citric acid or maleic acid.

For the preparation of pharmaceutical compositions, the new compounds of the present invention are mixed in the usual manner with appropriate pharmaceutical carriers, aroma, flavoring and coloring materials and formed, for example, into tablets or dragees or, with the addition of appropriate adjuvants, suspended or dissolved in water or in an oil, such as olive oil.

The following Examples illustrate the preparation of the compounds of the present invention:

EXAMPLE 1

Preparation of
2-methyl-4-(3-tert.-butylamino-2-hydroxy-propyloxy)-benzimidazole 7 g. 1-tert.-butylamino-2-hydroxy-3-(2-amino-3-nitrophenoxy)-propane were dissolved in ethanol and hydrogenated in the presence of platinum oxide at atmospheric pressure until the take-up of hydrogen ceases. The catalyst was then filtered off with suction and the filtrate was acidified with dilute hydrochloric acid and then evaporated to dryness. The crude 1-tert.-butylamino-2-hydroxy-3-(2,3-diaminophenoxy)-propane hydrochloride thus obtained was heated under reflux for 6 hours with 10 ml. glacial acetic acid and excess glacial acetic acid then removed under reduced pressure. The residue was dissolved in water and the solution obtained was rendered weakly alkaline with 1N sodium methylate solution and then left to stand for an hour at ambient temperature. It was thereafter acidified with dilute hydrochloric acid, the solution was evaporated, the residue was dissolved in a little hot ethanol and the solution was filtered, with the addition of active charcoal. After cooling, ether was added and the mixture was left to crystallize out in an icebath. In order to remove the last traces of sodium chloride, recrystallization from ethanol/ether might have to be repeated. There were obtained 4.3 g. 2-methyl-4-(3-tert.-butylamino-2-hydroxy-propyloxy)-benzimidazole in the form of its dihydrochloride; m.p. 204° – 206°C.

The 1-tert.-butylamino-2-hydroxy-3-(2-amino-3-nitrophenoxy)-propane used as starting material was prepared in the following manner:

25 ml. 4N aqueous sodium hydroxide solution was added to a mixture of 15.1 g. 2-amino-3-nitrophenol and 50 g. epichlorohydrin which has been heated to 75°C. and the reaction mixture was kept at 75°C. for 2 hours. The reaction mixture was diluted with 600 ml. water, then extracted several times with chloroform and the chloroform solution was dried over anhydrous sodium sulfate. Thereafter, it was evaporated to dryness and the solid residue was triturated with cold ethanol and filtered off with suction. There were obtained 17.5 g. 1-(2-amino-3-nitro-phenoxy-2,3-epoxy-propane; m.p. 80° – 82°C.

10.5 g. of the above 1-(2-amino-3-nitrophenoxy)-2,3-epoxy-propane were stirred for 30 hours at ambient temperature with 35 g. tert.-butylamine and 100 ml. ethanol. Subsequently, the reaction mixture was evaporated to dryness, the residue was dissolved in 200 ml. 2N hydrochloric acid, a small amount of undissolved material was filtered off with suction and the hydrochloric acid solution was shaken out several times with chlorofrom. 100 ml. 10N aqueous sodium hydroxide solution were then added to the aqueous acidic solution and the mixture extracted several times with ether. The ethereal extracts were dried over anhydrous sodium sulfate and then evaporated to about 100 ml., the base thereby separating out as a fine crystalline slurry by the use of ice cooling. There were obtained 10.5 g. 1-tert.-butylamino-2-hydroxy-3-(2-amino-3-nitrophenoxy)-propane; m.p. 75° – 77°C.

EXAMPLE 2

Preparation of
4-(3-tert.-butylamino-2-hydroxy-propyloxy)-benzimidazole

In a manner analogous to that described in Example 1, from 1-tert.-butylamino-2-hydroxy-3-(2,3-diaminophenoxy)-propane hydrochloride, with the use of 10 ml. formic acid (100%) instead of 10 ml. glacial acetic acid, there were obtained 3.9 g. 4-(3-tert.butylamino-2-hydroxy-propyloxy)- benzimidazole in the form of its dihydrochloride; m.p. 203° – 205°C.

EXAMPLE 3

Preparation of
2-methyl-4-(3-isopropylamino-2-hydroxypropyloxy)-benzimidazole 10.8 g. 1-isopropylamino-2-hydroxy-3-(2-amino-3-nitrophenoxy)-propane were hydrogenated at atmospheric pressure in ethanol in the presence of platinum oxide until the take-up of hydrogen ceases. The catalyst was then filtered off with suction and the filtrate was acidified with dilute hydrochloric acid and then evaporated to dryness. The crude 1-isopropylamino-2-hydroxy-3-(2,3-dimaminophenoxy)-propane hydrochloride so obtained was heated under reflux for 6 hours with 15 ml. glacial acetic acid and the reaction mixture then worked up in a manner analogous to that described in Example 1. There are obtained 5.3 g. 2-methyl-4-(3-isopropylamino-2-hydroxy-propyloxy)-benzimidazole in the form of its dihydrochloride; m.p. 208° – 210°C.

The 1-isopropylamino-2-hydroxy-3-(2-amino-3-nitrophenoxy)-propane (m.p. 108° – 110°C.) used as starting material can be obtained, in the manner described in Example 1, from 1-(2-amino-3-nitrophenoxy)-2,3-epoxy-propane, using 35 g. isopropylamine instead of 35 g. tert.-butylamine.

EXAMPLE 4

Preparation of
4-(3-isopropylamino-2-hydroxy-propyloxy)-benzimidazole

In a manner analogous to that described in Example 3, from 1-isopropylamino-2-hydroxy-3-(2,3-diaminophenoxy)-propane hydrochloride, there was obtained, with the use of 15 ml. formic acid (100%) instead of 15 ml. glacial acetic acid, 5.6 g. 4-(3-isopropylamino-2-hydroxy-propyloxy)-benzimidazole in the form of its dihydrochloride; m.p. 202° – 203°C.

The following tests were carried out to determine (a) the toxicity and (b) the cardiac β-receptor blocking activity of certain test compounds by determining the inhibition of the heart beat frequency increase induced by intravenous administration of isoprenalin.

The test compounds representative of the invention were the following:

| | |
|---|---|
| Compound I: | 4-(3-Isopropylamino-2-hydroxy-propyloxy)-benzimidazole |
| Compound II: | 4-(3-tert.-Butylamino-2-hydroxy-propyloxy)-benzimidazole |
| Compound III: | 2-Methyl-4-(3-isopropylamino-2-hydroxy-propyloxy)-benzimidazole |
| Compound IV: | 2-Methyl-4-(3-tert.-butylamino-2-hydroxy-propyloxy)-benzimidazole |

As comparison compounds there were included:

Compound A: 4-(2-Hydroxy-3-isopropylamino-propoxy)-acetanilide(Practolol)
Compound B: 1-Isopropylamino-3-(1-naphthoxy)-2-propanol (Propranolol)

droxy-α-[(isopropylamino)-methyl]-benzylalcohol) was injected intravenously at 1 μ/kg.

The results are set forth in terms of inhibition of isoprenalin tachycardia, and are set forth in the table below:

TABLE

Blocking of Isoprenalin Tachycardia in Wake Rabbits

| Test Substance | Acute Toxicity $LD_{50}$ Mouse mg/kg i.v. | Dosage mg/kg i.v. | Heartbeat Frequency $\bar{x} \pm \bar{s}_r$ | $DE_{250}$* mg/kg i.v. | $\dfrac{LD_{50}}{DE_{250}}$ |
|---|---|---|---|---|---|
| Control | — | Without Isoprenalin | 205 ± 9 | — | — |
| Control | — | with Isoprenalin | 338 ± 10 | — | — |
| Comparison Compound A (Practolol) | 69 | 0.5 | 307 ± 7 | 2.5 | 28 |
| | | 1.0 | 264 ± 9 | | |
| | | 2.0 | 250 ± 4 | | |
| | | 5.0 | 246 ± 7 | | |
| | | 10.0 | 217 ± 4 | | |
| | | 20.0 | 225 ± 6 | | |
| Compound B (Propanolol) | 17 | 0.01 | 342 ± 5 | 0.400 | 42 |
| | | 0.1 | 309 ± 9 | | |
| | | 0.25 | 259 ± 7 | | |
| | | 0.5 | 248 ± 6 | | |
| | | 1.0 | 210 ± 8 | | |
| | | 4.0 | 191 ± 6 | | |
| Compound I | 38 | 0.01 | 300 ± 11 | 0.09 | 422 |
| | | 0.05 | 292 ± 17 | | |
| | | 0.1 | 239 ± 6 | | |
| | | 0.5 | 228 ± 5 | | |
| | | 1.0 | 218 ± 11 | | |
| | | 5.0 | 219 ± 13 | | |
| Compound II | 28 | 0.01 | 286 ± 12 | 0.05 | 560 |
| | | 0.1 | 236 ± 6 | | |
| | | 1.0 | 244 ± 9 | | |
| | | 5.0 | 273 ± 11 | | |
| Compound III | 29 | 0.01 | 303 ± 17 | 0.17 | 170 |
| | | 0.05 | 318 ± 11 | | |
| | | 0.1 | 255 ± 9 | | |
| | | 1.0 | 234 ± 11 | | |
| | | 5.0 | 219 ± 14 | | |
| Compound IV | 34 | 0.01 | 289 ± 18 | 0.08 | 425 |
| | | 0.05 | 255 ± 7 | | |
| | | 0.1 | 248 ± 7 | | |
| | | 0.5 | 224 ± 8 | | |
| | | 1.0 | 211 ± 5 | | |
| | | 5.0 | 232 ± 5 | | |

*Interpolated dosage which limits the frequency increase to 250 beats/min.

These compounds were tested in the following manner:

a. The acute toxicity in mice when administered intravenously was measured and the $LD_{50}$ (=dosage at which 50% of the mice die) determined. The compounds, in dissolved form, were injected into the tail vein of five male and five female mice each in increasing dosages. The results (% of animals which died) were used, via programmed probability analysis, to determine the median lethal dosage ($LD_{50}$). The results were set forth in the table below.

b. The β-receptor blocking activity of the test compounds was tested on wake rabbits weighing between 2 to 3.5 kg. and kept in wooden cages. EKG-electrodes were inserted into the hind quarters of the rabbits s.c. (II. lead) and the heart frequency was measured using an integrator (15 seconds) as a digital value. The test compounds were then infused through a small tube to the ear vein of the rabbits over a period of 15 minutes. 30 Minutes after the infusion isoprenalin (3,4-dihy- The above data show dosage that the inventive compounds are already effective at a dosage much smaller than those required of the comparison substances and the "therapeutic breadth" is much greater for the claim compounds as measured by the ratio of $LD_{50}$ to $DE_{250}$ as set forth in the last column of the foregoing table. It will thus be seen that the inventive compounds provide a far greater margin of safety in that the margin between the dosage which is toxic to mice, and the dosage giving tachycardia blocking, is very large and substantially larger than the margin provided by the comparison compound. Thus, the dosage at which the test compounds limited the heartbeat frequency increase induced by isoprenalin to 250 beats per minute (as determined by interpolation and set forth in the table as $De_{250}$) to the $LD_{50}$ dosage was in the order of at least 170 and normally about 400, whereas for the prior art compounds the ratio is only 28 and 42. Thus, the lethal dosage is so much higher than the dosage effective for tachycardia blocking that the instant compounds are obviously so much safer than the prior art materials.

The compounds according to the present invention are thus unexpectedly superior in effectiveness to known compounds and thus present a valuable contribution to the art.

The dosage of the novel compounds of the present invention depend on the age, weight, and condition of the patient being treated. Generally speaking, for adult oral administration, the preferred unit dosage of active compound with suitable pharmaceutical diluent or lubricant is 1 mg. - 40 mg. 4 times a day. In general the oral dosage is 20 - 40 mg., whereas the intravenous dosage is generally 1 - 5 mg., 4 times a day.

Thus, the applied dosage of the novel compounds can be from about 4 to 160 mg per day per 75 kg of body weight of the patient being treated.

For the preparation of pharmaceutical compositions, at least one of the new compounds according to the present invention is mixed with appropriate solid or liquid pharmaceutical diluents or carriers and, if desired, also with odoriferous, flavoring and coloring material and then formed into, for example, tablets or dragees or, with the addition of appropriate adjuvants, suspended or dissolved in water or oil, for example in olive oil.

The new compounds according to the present invention of general formula (I) and the salts thereof can be administered enterally or parentally in solid or liquid form. As injection medium, it is preferred to use water which contains the conventional additives for injection solutions, for example stabilizing agents, solubilizing agents or buffers. Additives of this kind include, for example, tartrate and citrate buffers, ethanol, complex-forming agents (such as ethylenediamine-tetraacetic acid and the non-toxic salts thereof), and high molecular weight polymers (such as polyethylene oxide) for viscosity regulation. Solid carrier materials include, for example, starch, lactose, mannitol, methyl cellulose, talc, highly-dispersed silicic acids, high molecular weight fatty acids (such as stearic acid), gelatine, agar-agar, calcium phosphate, magnesium stearate, animal and vegetable fats and solid high molecular weight polymers (such as polyethylene glycols); compositions which are suitable for oral administration can, if desired, contain flavoring and sweetening agents.

For preparing compounds such as tablets and other compressed formulations, the compounds can include any compatible and edible tableting material used in pharmaceutical practice as for example, corn starch, lactose, stearic acid, magnesium stearate, talc, methyl cellulose and the like.

Similarly the compounds of the present invention can be mixed with suitable adjuvants for the preparation of resorbable hard gelatin or soft capsules utilizing conventional pharmaceutical practices.

Further, the compounds can be employed in the form of their solutions or suspensions suitable for parenteral administration.

It will be appreciated that the instant specification and examples are set forth by way of illustration and not limitation, and that various modifications and changes may be made without departing from the spirit and scope of the present invention.

What is claimed is:

1. 4-Hydroxy-benzimidazole compound of the formula:

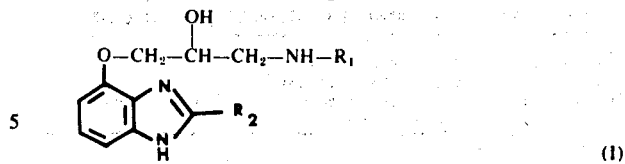

wherein
 $R_1$ is straight-chained or branched alkyl of up to 6 carbon atoms and
 $R_2$ is hydrogen atom or lower alkyl of up to 3 carbon atoms
and the pharmacologically compatible salts thereof.

2. 4-Hydroxy-benzimidazole compound as claimed in claim 1 wherein $R_1$ is branched alkyl.

3. 4-Hydroxy-benzimidazole compound as claimed in claim 1 wherein $R_1$ is alkyl up to 4 carbon atoms.

4. 4-Hydroxy-benzimidazole compounds as claimed in claim 1 wherein $R_1$ is branched alkyl of 3 to 4 carbon atoms.

5. 4-Hydroxy-benzimidazole compound as claimed in claim 1 wherein $R_2$ is hydrogen.

6. 4-Hydroxy-benzimidazole compound as claimed in claim 1 wherein $R_2$ is methyl.

7. 4-Hydroxy-benzimidazole compound as claimed in claim 1 designated 2-methyl-4-(3-tert.-butylamino-2-hydroxypropyloxy)-benzimidazole.

8. 4-Hydroxy-benzimidazole compound as claimed in claim 1 designated 4-(3-tert.-butylamino-2-hydroxypropyloxy)-benzimidazole.

9. 4-Hydroxy-benzimidazole compound as claimed in claim 1 designated 2-methyl-4-(3-isopropylamino-2-hydroxypropyloxy)-benzimidazole.

10. 4-Hydroxy-benzimidazole compound as claimed in claim 1 designated 4-(3-isopropylamino-2-hydroxypropyloxy)-benzimidazole.

11. Therapeutic composition having adrenergic β-receptor inhibiting activity comprising a pharmaceutically acceptable carrier and an effective amount of at least one 4-hydroxy-benzimidzole compound as claimed in claim 1.

12. Method for the treatment or prophylaxis of cardiac and circulatory diseases which method comprises administering to the afflicted subject a therapeutically effective amount of a 4-hydroxy-benzimidazole compound of the formula

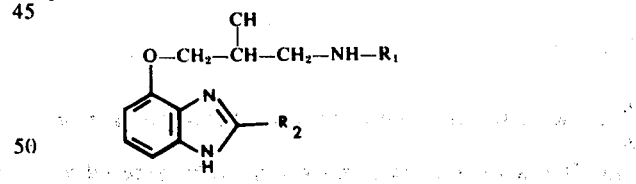

wherein
 $R_1$ is straight-chained or branched alkyl of up to 6 carbon atoms and
 $R_2$ is hydrogen atom or lower alkyl of up to 3 carbon atoms
and the pharmacologically compatible salts thereof.

13. Method as claimed in claim 12 wherein the compound is applied at a dosage of about 4 to 160 mg. per day per 75 kg. of body weight of said subject.

14. Method as claimed in claim 12 wherein said compound is selected from the group consisting of 2-methyl-4-(3-tert.-butylamino-2-hydroxy-propyloxy)-benzimidazole, 4-(3-tert.-butylamino-2hydroxy-propyloxy)-benzimidazole, 2-methyl-4-(3-isopropylamino-2-hydroxy-propyloxy)-benzimidazole, and 4-(3-isopropylamino-2hydroxy-propyloxy)-benzimidazole.

* * * * *

UNITED STATES PATENT AND TRADEMARK OFFICE
CERTIFICATE OF CORRECTION

PATENT NO. : 3,982,012
DATED : September 21, 1976
INVENTOR(S) : Erich Fauland; Wolfgang Kampe; Max Thiel; Wolfgang Bartsch; Wolfgang Schaumann It is certified that error appears in the above-identified patent and that said Letters Patent are hereby corrected as shown below:

Column 1, line 68 in the formula

"NO$_2$" should read --NH$_2$--;

Column 2, line 43 in the formula second "NH$_2$" should read --NO$_2$--;

Column 3, line 60 "chlorofrom" should read --chloroform--;

Column 8, line 45 in formula top line

"CH" should read --OH--.

Signed and Sealed this

First Day of March 1977

[SEAL]

Attest:

RUTH C. MASON
Attesting Officer

C. MARSHALL DANN
Commissioner of Patents and Trademarks